United States Patent
Kakishita et al.

(10) Patent No.: US 11,176,668 B2
(45) Date of Patent: Nov. 16, 2021

(54) IMAGE DIAGNOSIS ASSISTING APPARATUS, IMAGE DIAGNOSIS ASSISTING METHOD AND SAMPLE ANALYZING SYSTEM

(71) Applicant: Hitachi High-Technologies Corporation, Tokyo (JP)

(72) Inventors: Yasuki Kakishita, Tokyo (JP); Hideharu Hattori, Tokyo (JP); Kenko Uchida, Tokyo (JP); Sadamitsu Aso, Tokyo (JP); Toshinari Sakurai, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 134 days.

(21) Appl. No.: 16/323,808

(22) PCT Filed: Aug. 28, 2017

(86) PCT No.: PCT/JP2017/030817
§ 371 (c)(1),
(2) Date: Feb. 7, 2019

(87) PCT Pub. No.: WO2018/051777
PCT Pub. Date: Mar. 22, 2018

(65) Prior Publication Data
US 2019/0172206 A1   Jun. 6, 2019

(30) Foreign Application Priority Data
Sep. 13, 2016   (JP) .............. JP2016-178245

(51) Int. Cl.
*G06T 7/00* (2017.01)
*A61B 5/00* (2006.01)
(Continued)

(52) U.S. Cl.
CPC .......... *G06T 7/0014* (2013.01); *A61B 5/0059* (2013.01); *A61B 5/7267* (2013.01);
(Continued)

(58) Field of Classification Search
CPC .......... G16H 30/00; G16H 30/40; G06T 7/11; G06T 2207/10056; G06T 2207/30024;
(Continued)

(56) References Cited

U.S. PATENT DOCUMENTS 10,395,368 B2 * 8/2019 Berezhna ............... G01N 33/52
2011/0057946 A1 3/2011 Yamamoto
(Continued)

FOREIGN PATENT DOCUMENTS

JP   2010-203949 A   9/2010
JP   2011-95921 A    5/2011
(Continued)

OTHER PUBLICATIONS

International Search Report (PCT/ISA/210) issued in PCT Application No. PCT/JP2017/030817 dated Nov. 14, 2017 with English translation (three (3) pages).
(Continued)

*Primary Examiner* — Wesley J Tucker
(74) *Attorney, Agent, or Firm* — Crowell & Moring LLP

(57) ABSTRACT

Reaction values indicating based on which areas in an input image a plurality of identification results representing the states of cells or tissues are judged are calculated, and differences between a plurality of reaction values are obtained to thereby calculate the degree to which cells or tissues in an area of interest likely are in each state. Thereby, each state of cells or tissues can be visualized at an accurate position in an area of interest; therefore, diagnostic assistance to pathologist becomes possible.

9 Claims, 12 Drawing Sheets

(51) Int. Cl.
*G16H 30/00* (2018.01)
*G06T 7/11* (2017.01)
*G06K 9/00* (2006.01)

(52) U.S. Cl.
CPC ............ *G06K 9/00147* (2013.01); *G06T 7/11* (2017.01); *G06T 7/97* (2017.01); *G16H 30/00* (2018.01); *A61B 5/0013* (2013.01); *A61B 5/0022* (2013.01); *G06T 2207/10056* (2013.01); *G06T 2207/20224* (2013.01); *G06T 2207/30024* (2013.01)

(58) Field of Classification Search
CPC ......... G06T 2207/20021; G06T 7/0012; G06T 7/0014; G06T 7/97; G06T 2207/20224; G06T 2207/20081; G06T 2207/20084; G06T 2207/20076; A61B 5/0013; A61B 5/7267; A61B 5/0059; A61B 5/0022; A61B 5/0033; A61B 5/145; G06K 9/00147

See application file for complete search history.

(56) References Cited

U.S. PATENT DOCUMENTS

| | | | |
|---|---|---|---|
| 2012/0004514 A1 | 1/2012 | Marugame | |
| 2012/0076372 A1 | 3/2012 | Nishimura et al. | |
| 2014/0112569 A1* | 4/2014 | Liu | G06K 9/52 382/133 |
| 2015/0111217 A1* | 4/2015 | Hendriks | G01N 33/57492 435/6.19 |
| 2017/0178361 A1* | 6/2017 | Berezhna | G01N 15/1475 |
| 2019/0137497 A1* | 5/2019 | Thorne | G01N 33/57407 |
| 2019/0259158 A1* | 8/2019 | Rimm | G06T 7/41 |
| 2019/0286790 A1* | 9/2019 | Kaigala | G16H 50/30 |

FOREIGN PATENT DOCUMENTS

| | | |
|---|---|---|
| JP | 2012-8027 A | 1/2012 |
| WO | WO 2011/129176 A1 | 10/2011 |
| WO | WO 2013/022688 A1 | 2/2013 |

OTHER PUBLICATIONS

Japanese-language Written Opinion (PCT/ISA/237) issued in PCT Application No. PCT/JP2017/030817 dated Nov. 14, 2017 (three (3) pages).

Extended European Search Report issued in European Application No. 17850681.2 dated Mar. 27, 2020 (eight (8) pages).

* cited by examiner

F I G . 1
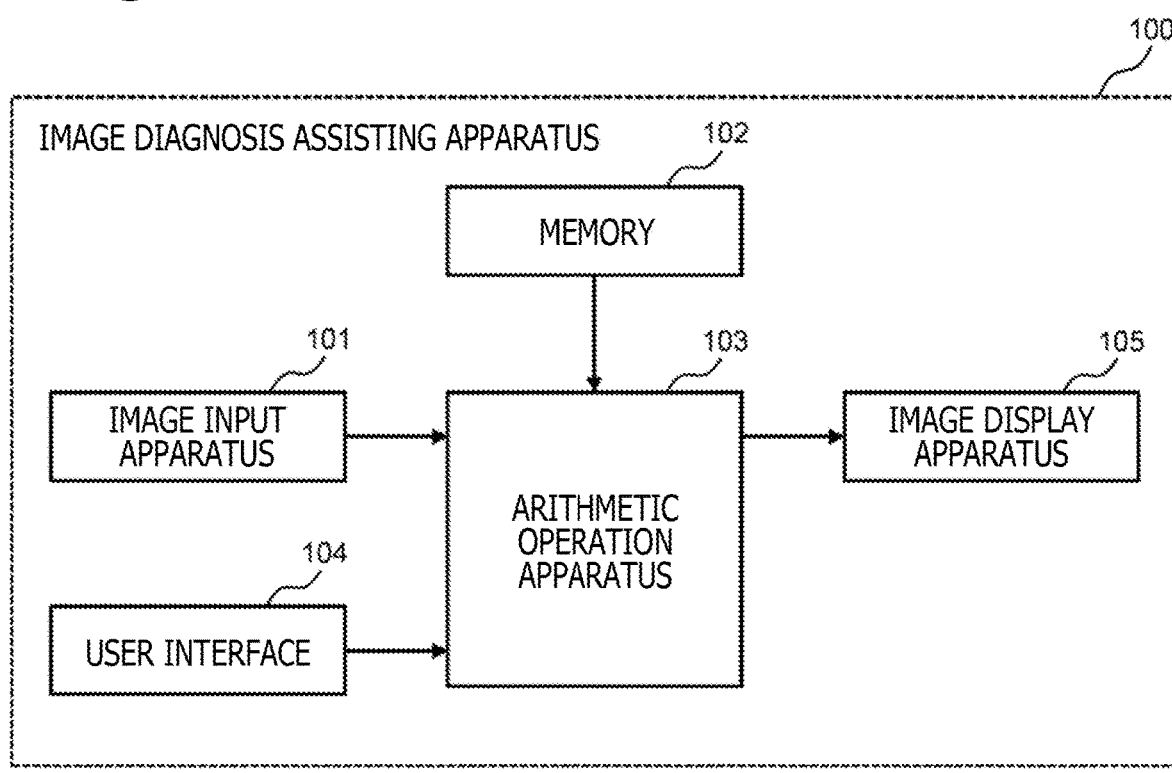

IMAGE DIAGNOSIS ASSISTING APPARATUS, IMAGE DIAGNOSIS ASSISTING METHOD AND SAMPLE ANALYZING SYSTEM

TECHNICAL FIELD

The present invention relates to an image diagnosis assisting apparatus, an image diagnosis assisting method and a sample analyzing system, and in particular is suited for application to an image diagnosis assisting apparatus that automatically identifies the states of cells or tissues based on a cell image or a tissue image, and displays a result of the identification.

BACKGROUND ART

In recent years, a shortage of pathologists has become a problem along with increase in the number of cancer patients. As a solution to the problem, a technology called digital pathology that performs diagnostic assistance or remote diagnosis using digitized pathological images has been attracting attention (see, Patent Document 1). This is a technology that automatically identifies pathological tissues using high magnification pathological images and low magnification pathological images.

PRIOR ART DOCUMENT

Patent Document

Patent Document 1: JP-2010-203949-A

SUMMARY OF THE INVENTION

Problem to be Solved by the Invention

In the above-mentioned conventional techniques, rectangular areas of interest are selected out of pathological images, and an identification result is displayed for each area of interest. However, only a particular identification result is displayed in an area of interest, and the states of cells or tissues in the area of interest cannot be displayed. Even if an identification result in the unit of pixel is obtained by identifying cells or tissues while shifting the area of interest pixel by pixel, and identification results are displayed at an anchor position such as the center of the area of interest, it is difficult to display the cell or tissue state of the anchor position accurately since the identification results are results obtained through general judgment based on images around the anchor.

The present invention has been made in view of the above-mentioned circumstances, and proposes an image diagnosis assisting apparatus, an image diagnosis assisting method and a sample analyzing system that visualize the states of cells or tissues at accurate positions in an area of interest and enable sufficient diagnostic assistance.

Means for Solving the Problem

To solve such a problem, in the present invention, a local area feature amount calculating unit that calculates a local area feature amount from an input image; an identifying unit that performs a plurality of identification processes using the local area feature amount; a reaction value calculating unit that calculates a plurality of reaction values indicating based on which unit area in the input image each identification result is judged, using a calculation result of the local area feature amount and a result of the plurality of identification processes; and a reaction value difference calculating unit that calculates differences between the plurality of reaction values are included.

In addition, in the present invention, a staining shade classification step of classifying, by an arithmetic operation unit, an input image according to staining shade; a local area feature amount calculation step of calculating, by the arithmetic operation unit, a local area feature amount from the input image; an identification step of performing, by the arithmetic operation unit, a plurality of identification processes using the local area feature amount; a reaction value calculation step of calculating, by the arithmetic operation unit, a plurality of reaction values indicating based on which unit area in the input image each identification result is judged, using a calculation result of the local area feature amount and a result of a plurality of identification processes; and a reaction value difference calculation step of calculating, by the arithmetic operation unit, differences between a plurality of reaction values are included.

In addition, in the present invention, a local area feature amount calculation step of calculating, by an arithmetic operation unit, a local area feature amount from an input image; an identification step of performing, by the arithmetic operation unit, a plurality of identification processes using the local area feature amount; a reaction value calculation step of calculating, by the arithmetic operation unit, a plurality of reaction values indicating based on which unit area in the input image each identification result is judged, using a calculation result of the local area feature amount and a result of a plurality of identification processes; and a reaction value difference calculation step of calculating, by the arithmetic operation unit, differences between a plurality of reaction values are included.

In addition, in the present invention, a local area feature amount calculating unit that calculates a local area feature amount from an input image; an identifying unit that performs a plurality of identification processes using the local area feature amount; a reaction value calculating unit that calculates a plurality of reaction values indicating based on which unit area in the input image each identification result is judged, using a calculation result of the local area feature amount and a result of the plurality of identification processes; a reaction value difference calculating unit that calculates differences between the plurality of reaction values; a sample collecting unit that collects a sample based on the calculated information; and an analyzing unit that performs analysis of the sample collected by the sample collecting unit are included.

Effect of the Invention

According to the present invention, the states of cells or tissues are visualized at accurate positions in an area of interest, and sufficient diagnostic assistance becomes possible.

BRIEF DESCRIPTION OF THE DRAWINGS

FIG. 1 is a hardware configuration diagram of an image diagnosis assisting apparatus according to a first embodiment.

DESCRIPTION OF EMBODIMENTS

Figure 2:
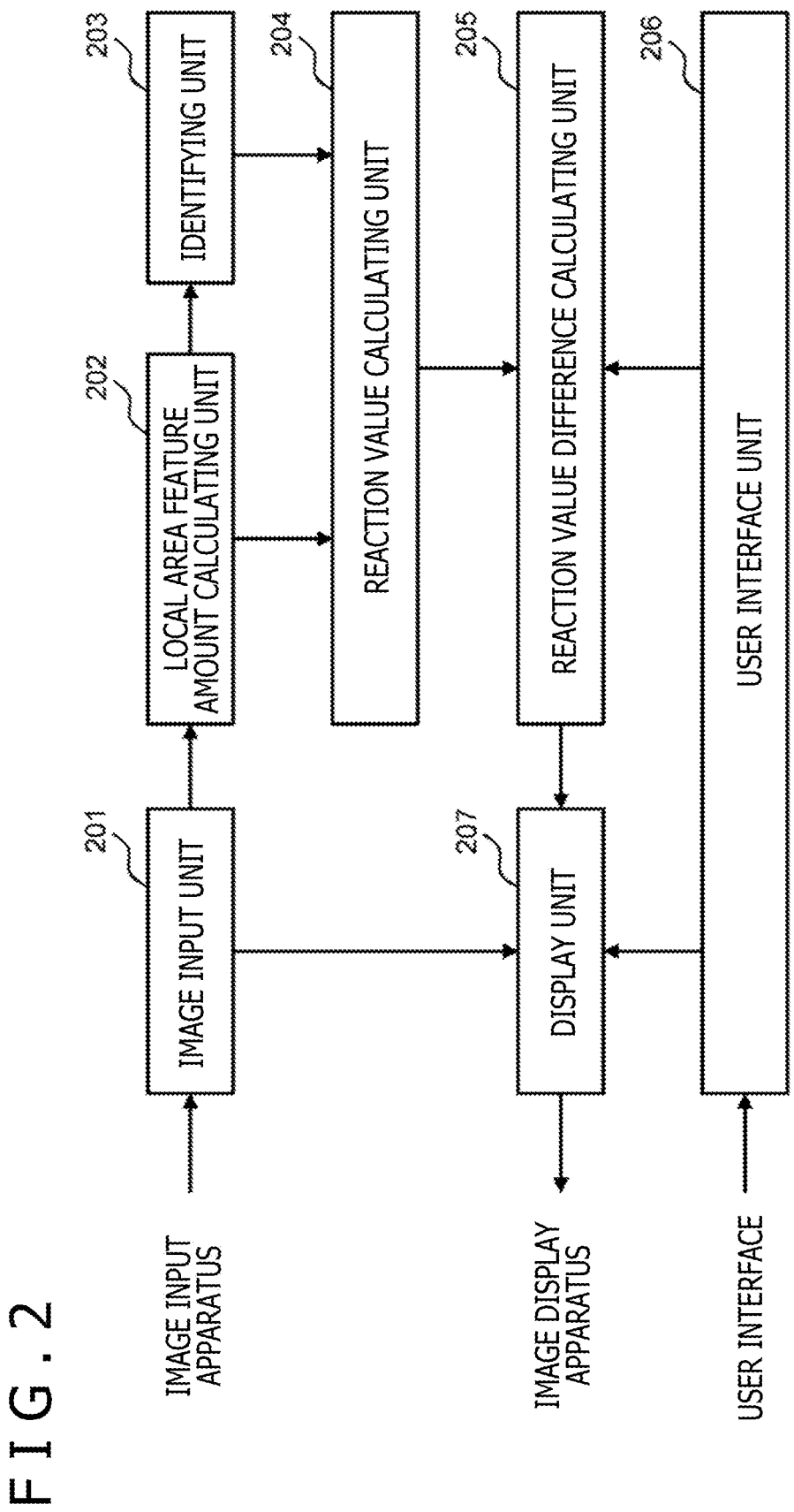
FIG. 2 is a block diagram of an arithmetic operation apparatus according to the first embodiment.

Hereinafter, embodiments of the present invention are described in detail with reference to the figures.

(1) Configuration of Image Diagnosis Assisting Apparatus According to First Embodiment FIG. 1 is a hardware configuration diagram of an image diagnosis assisting apparatus 100 according to a first embodiment. The image diagnosis assisting apparatus 100 includes an image input apparatus 101, a memory 102, an arithmetic operation apparatus 103, a user interface 104 and an image display apparatus 105.

The image input apparatus 101 receives an input of a virtual slide or a microscopic image. The memory 102 stores therein a coefficient group to be used in feature amount extraction and a coefficient group to be used in identification processes or input images and calculated reaction values, for example. In the present embodiment, the coefficient groups to be used in feature amount extraction and in identification processes are called "weights." The arithmetic operation apparatus 103 is a CPU, an FPGA or the like, and performs extraction of local area feature amounts or identification processes, or calculation of reaction values, for example.

The user interface 104 receives manipulation information from a user using a keyboard or a mouse. The image display apparatus 105 is a display apparatus, for example. This image display apparatus 105 displays information to a user via the arithmetic operation apparatus 103. The image diagnosis assisting apparatus 100 may have a built-in communication apparatus for performing communication with the outside or may separately have a communication apparatus that is externally attached thereto, although illustration of such a communication apparatus is omitted.

FIG. 2 depicts functional blocks of the image diagnosis assisting apparatus 100 depicted in FIG. 1. An image input unit 201 receives an input of a cell or tissue image from the image input apparatus 101. A local area feature amount calculating unit 202 calculates feature amounts of local areas for the image input through the image input unit 201.

An identifying unit 203 has a plurality of identifying devices, and uses the local area feature amounts output by the local area feature amount calculating unit 202 to output a result of identification of a plurality of states. A reaction value calculating unit 204 uses the feature amounts and identification result output by the local area feature amount calculating unit 202 and identifying unit 203 to calculate a plurality of reaction values indicating based on which unit area in the input image each identification result is judged.

A reaction value difference calculating unit 205 performs processes such as obtaining difference between or combining the plurality of reaction values output by the reaction value calculating unit 204. Combining is adding, multiplying, obtaining the logical sum, obtaining the logical product or the like. A result of the process of obtaining difference and combining is called reaction value difference information. This reaction value difference calculating unit 205 receives, from a user interface unit 206, reaction value specifying information to be used in the process of obtaining difference, combining or the like.

The user interface unit 206 receives manipulation information from a user, and outputs, to the reaction value difference calculating unit 205 and a display unit 207, the reaction value specifying information to be used in the process of obtaining difference, combining or the like. The display unit 207 determines information to be displayed on the image display apparatus 105.

The display unit 207 receives inputs of the input image from the image input unit 201, the reaction value difference information from the reaction value difference calculating unit 205, and the user manipulation information from the user interface unit 206, and displays the input image and a reaction value difference image according to the manipulation information, switching from one of them to the other, or displays an image obtained by superimposing the input image and reaction value difference information.

Hereinafter, the local area feature amount calculating unit 202, identifying unit 203, reaction value calculating unit 204 and reaction value difference calculating unit 205 are explained in detail.

Next, the local area feature amount calculating unit 202 is explained. The local area feature amount calculating unit 202 uses weights for extracting feature amounts such as local colors, luminance or shapes of the input image stored in the memory 102 to thereby obtain a feature amount of each pixel or small area unit in the input image. This is called a "local area feature amount." Although in the present embodiment, a method in which convolution of a weight into input data is performed is explained as an exemplary local area feature amount calculation method, a local area feature amount may be obtained by another method such as HOG (Histogram of Oriented Gradients).

Figure 3:
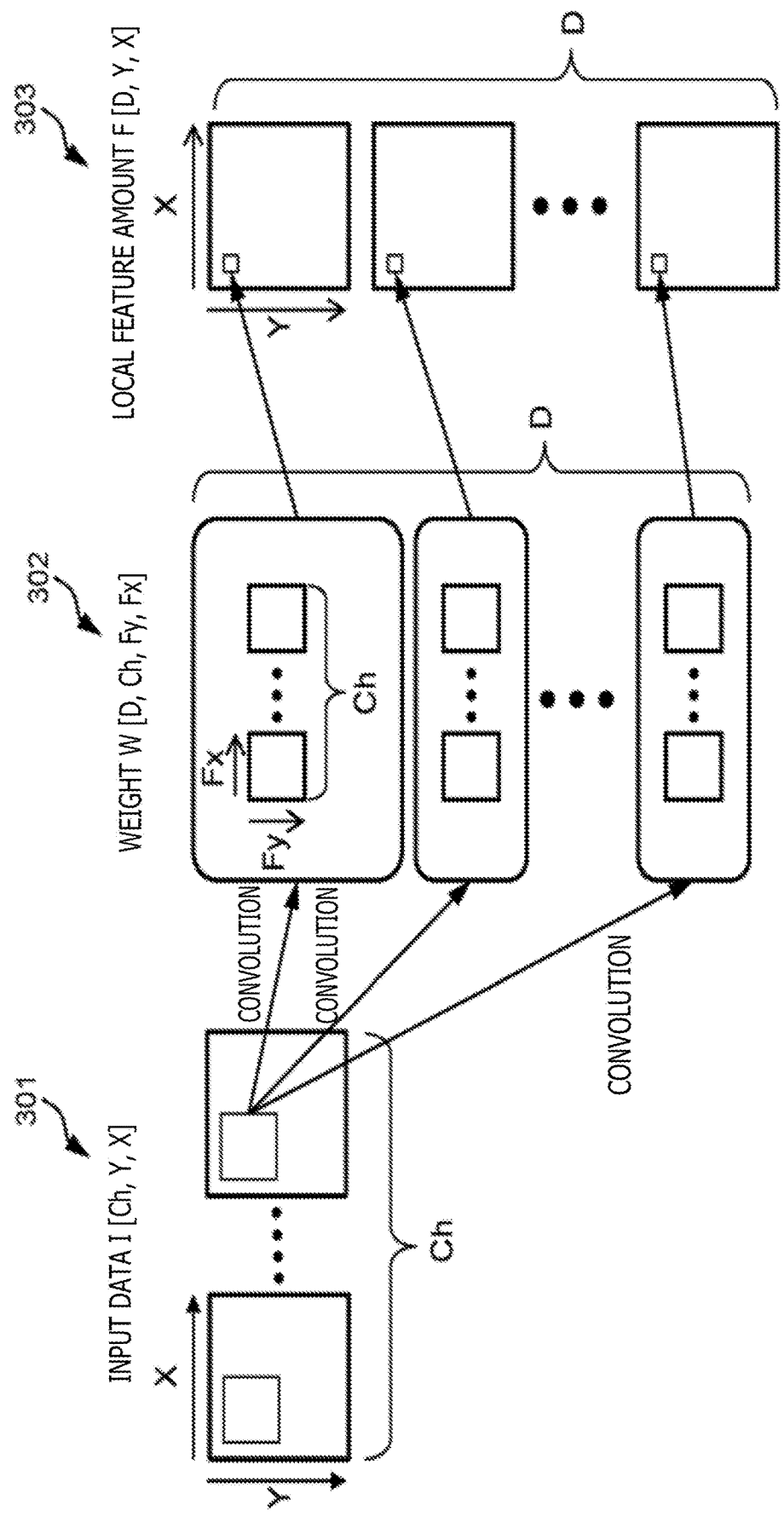
FIG. 3 depicts an exemplary local area feature amount calculation process.

FIG. 3 depicts an exemplary local area feature amount calculation process. Input data 301 is a three-dimensional array having a channel Ch, vertical position Y and horizontal position X dimensions. A weight 302 includes a plurality of weights for extracting a plurality of feature amounts from the input data 301. Because of this, the weight 302 is a four-dimensional array having a feature amount number D dimension in addition to the channel Ch, vertical position Fy and horizontal position Fx dimensions. The weight 302 to be used may be one designed manually or may be one learned through machine learning using so-called AI (Artificial Intelligence), for example.

Note that although, in the present embodiment, it is assumed that weights to be used in local area feature amount calculation are weights learned through machine learning, the weights may be updated using input images by techniques such as so-called unsupervised learning, for example. The above-mentioned updating of the weights is not limited to that executed in an apparatus, but may be performed in a manner such as sending information to a server or the like via a communication apparatus and receiving a result of updating performed at the server.

A local feature amount 303, which is output data, is a three-dimensional array having a feature amount number D, vertical position Y and horizontal position X dimensions. In the example depicted in FIG. 3, the local feature amount 303 is calculated by repeating a process of multiplying the weight 302 for local areas in the input data 301 while shifting the local area. One element of the local feature amount 303, which is output data, is obtained by using Formula (1) like the one depicted below.

$$F(d, y, x) = G\left(\sum_{ch=0}^{Ch}\sum_{f_y=0}^{F_y}\sum_{f_x=0}^{F_x}(I(ch, y+f_y, x+f_x) \times W(d, ch, f_y, f_x))\right) \quad (1)$$

F: Local area feature amount
I: Input data
W: Weight
G: Nonlinear function or linear function
d: Feature amount number (0, 1, . . . , D)
y: Vertical position in the input data (0, 1, . . . , Y)
x: Horizontal position in the input data (0, 1, . . . , X)
ch: Channel of the input data (0, 1, . . . , Ch)
fy: Vertical position in the filter (0, 1, . . . , Fy)
fx: Horizontal position in the filter (0, 1, . . . , Fx)

F(d, y, x) indicates a feature amount number d and the values of a local feature amount 303 at a vertical position y and a horizontal position x. F(d, y, x) is calculated by multiplying each element of the input data 301 among channels 0 to Ch, vertical positions y to y+fy, and horizontal positions x to x+fx by each element w (d, ch, fy, fx) of the weight 302 and then obtaining the sum total of them.

Note that local area feature amounts can be obtained in a stratified manner. If local area feature amounts are obtained in a stratified manner, an output from a preceding layer serves as an input in the following layer.

The identifying unit 203 is explained. The identifying unit 203 uses the local area feature amounts output by the local area feature amount calculating unit 202 to perform identification of a plurality of states. The identifying unit 203 uses a weight for local area feature amounts stored in the memory 102 to calculate the likelihood of each state. The likelihood is a numerical value representing the degree to which an area of interest likely is in each state. Although in a manner explained as an exemplary identification method in the present embodiment, the likelihood of each state is calculated by multiplying a local area feature amount by a weight and summing the resultant values, it may be identified by other methods such as a decision tree, for example.

Figure 4:
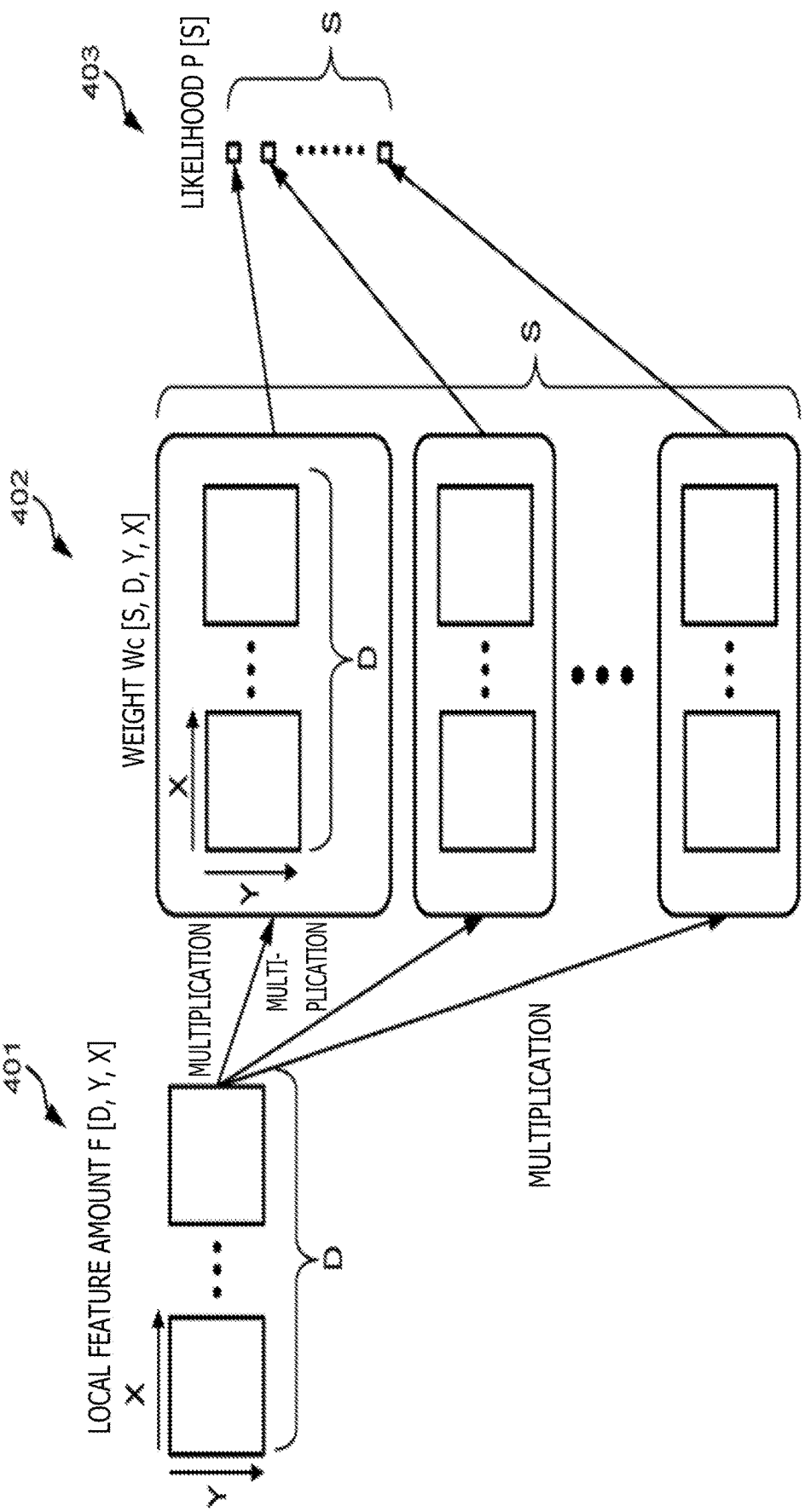
FIG. 4 depicts an exemplary procedure of an identification process.

FIG. 4 depicts an exemplary procedure of an identification process. A local area feature amount F401 is a local area feature amount obtained at the local area feature amount calculating unit 202, and is a three-dimensional array having a feature amount number D, vertical position Y and horizontal position X dimensions.

A weight Wc402 is a four-dimensional array having a feature amount index D, vertical position Y, horizontal position X and state S dimensions. The weight used may be one designed manually or may be one learned through machine learning.

Note that although, in the present embodiment, it is assumed that weights to be used in identification are weights learned through machine learning, the weights may be updated using input images by techniques such as so-called semi-supervised learning, for example. In addition, the updating of the weights is not limited to that executed in an apparatus, but may be performed in a manner such as sending information to a server or the like via a communication apparatus and receiving a result of updating performed at the server.

Likelihood P403 is a one-dimensional array having a state S dimension. In the example depicted in FIG. 4, the likelihood P403 of each state is calculated by multiplying the local area feature amount F401 by a weight Wc402 for each state. One element of the likelihood P403 is obtained by using Formula (2) like the one depicted below.

$$P(s) = G\left(\sum_{d=0}^{D}\sum_{y=0}^{Y}\sum_{x=0}^{X}(F(d, y, x) \times Wc(s, d, y, x))\right) \quad (2)$$

P: Identification result
F: Local area feature amount
Wc: Weight
G: Nonlinear function or linear function
s: State number (0, 1, . . . , S)
d: Feature amount number (0, 1, . . . , D)
y: Vertical position in the input data (0, 1, . . . , Y)
x: Horizontal position in the input data (0, 1, . . . , X)

P(s) indicates the likelihood P403 for the state s, and is calculated by multiplying each element of the local area feature amount F401 by each element of the weight Wc402 and then obtaining the sum total of them.

Next, the reaction value calculating unit 204 is explained. The reaction value calculating unit 204 calculates, for each pixel or small area unit, a reaction value indicating based on which unit area in the input image each identification result is judged. The reaction value is calculated from a weight and each output of the local area feature amount calculating unit 202 and the identifying unit 203. Here, an exemplary reaction value calculation method is described.

Figure 5:
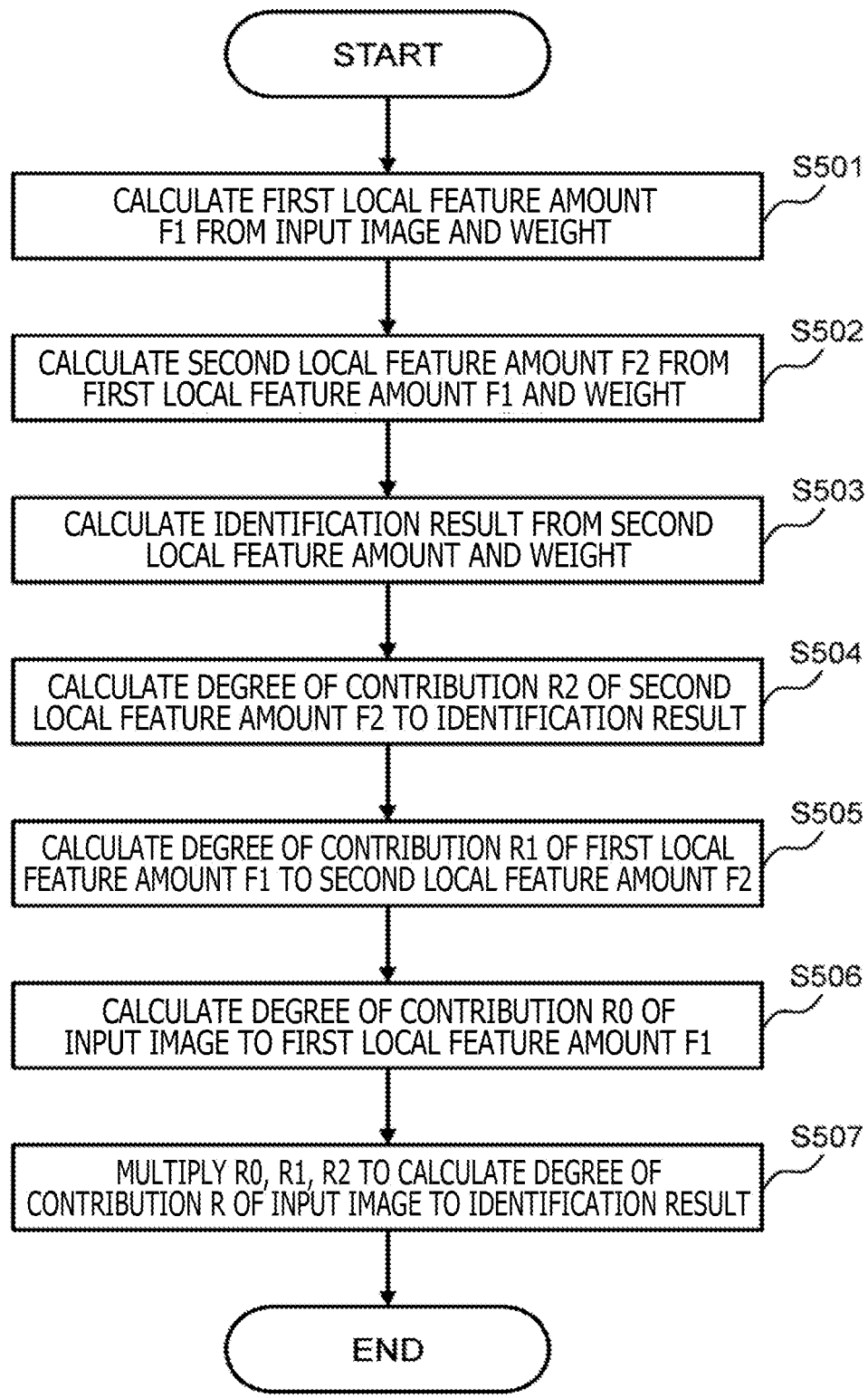
FIG. 5 depicts an exemplary reaction value calculation flow.
Figure 10:
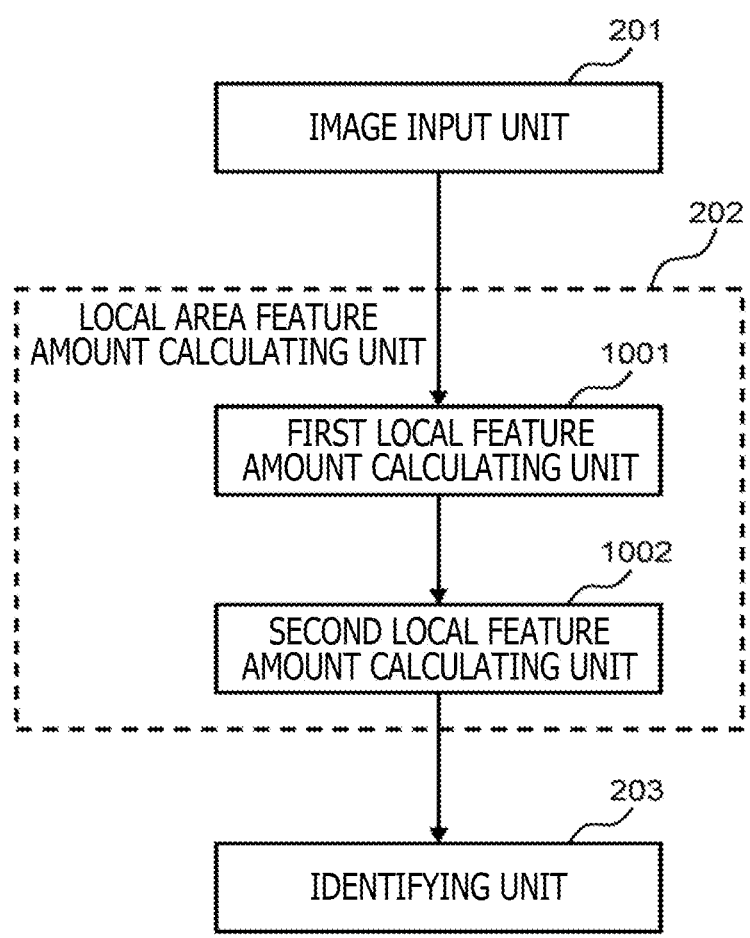
FIG. 10 depicts an exemplary local area feature amount calculating unit.

FIG. 5 depicts an exemplary procedure of calculating a reaction value. To make explanation easy, it is assumed that the local area feature amount calculating unit 202 and the identifying unit 203 like the ones depicted in FIG. 10 are provided. That is, the local area feature amount calculating unit has a stratified configuration.

First, at Step S501, a first local feature amount calculating unit 1001 calculates a first local feature amount from an input image. On the other hand, at Step S502, a second local feature amount calculating unit 1002 calculates a second local feature amount from the first local feature amount.

At Step S503, the identifying unit 203 uses the second local feature amount to perform identification, and obtains an identification result. At Step S504, the degree of contribution R2 of the second local feature amount F2 to the identification result is calculated. A degree of contribution is a value indicating to what degree each element of an input contributed to increase in an output value. That is, the degree of contribution R2 indicates to what degree each element of the second local feature amount F2 contributed to increase in the identification result. The degree of contribution R2 is obtained by using Formula (3) like the one depicted below.

$$R2(s,d,y,x) = F2(d,y,x) \times Wc(s,d,y,x) \quad (3)$$

R2: Degree of contribution of the second layer local feature amount to the identification result
F2: Second layer local feature amount
Wc: Weight at the identifying unit
s: State number (0, 1, . . . , S)
d: Feature amount number (0, 1, . . . , D)
y: Vertical position (0, 1, . . . , Y)

x: Horizontal position (0, 1, ..., X)

Formula (3) indicates the inner product of the second layer local feature amount F2 and the weight Wc at the identifying unit. The larger the value of R2 is, the higher the degree of contribution to increase in the likelihood of each state is.

At Step S505, the degree of contribution R1 of the first local feature amount F1 to the second local feature amount F2 is calculated. The degree of contribution R1 is calculated by using Formula (4) like the one depicted below.

$$R1(d2, d1, y, x) = \sum_{fy=0}^{Fy} \sum_{fx=0}^{Fx} F1(d1, y, x) \times W2(d2, d1, fy, fx) \quad (4)$$

R1: Degree of contribution of the first layer local feature amount to the degree of contribution R2
F1: First layer local feature amount
W2: Second layer weight
d2: Second layer feature amount number (0, 1, ..., D2)
d1: First layer feature amount number (0, 1, ..., D1)
y: Vertical position (0, 1, ..., Y)
x: Horizontal position (0, 1, ..., X)
fy: Vertical position in the filter (0, 1, ..., Fy)
fx: Horizontal position in the filter (0, 1, ..., Fx)

The above-mentioned Formula (4) indicates the local inner product of the first local feature amount F1 and the weight W2 at the second local feature amount calculating unit 1002. The larger the value of R1 is, the higher the degree of contribution to increase in the second local feature amount F2 is.

At Step S506, the reaction value calculating unit 204 calculates the degree of contribution R0 of the input image to the first local feature amount F1. The degree of contribution R0 is represented by using Formula (5) like the one depicted below.

$$R0(d1, ch, y, x) = \sum_{fy=0}^{Fy} \sum_{fx=0}^{Fx} I(ch, y, x) \times W1(d1, ch, fy, fx) \quad (5)$$

R0: Degree of contribution of the input image to the degree of contribution R1
I: Input image
W1: First layer weight
d1: First layer feature amount number (0, 1, ..., D1)
ch: Channel of the input image (0, 1, ..., Ch)
y: Vertical position (0, 1, ..., Y)
x: Horizontal position (0, 1, ..., X)
fy: Vertical position in the filter (0, 1, ..., Fy)
fx: Horizontal position in the filter (0, 1, ..., Fx)

Formula (5) indicates the local inner product of the input image I and the weight W1 at the first local feature amount calculating unit 1001. The larger the value of R0 is, the higher the degree of contribution to increase in the local feature amount F1 is.

At Step S507, the reaction value calculating unit 204 uses Formula (6) like the one depicted below to multiply the values of the degrees of contribution R2, R1, R0 obtained at Steps S504 to S506.

$$R(s, y, x) = \quad (6)$$

-continued
$$\sum_{d2=0}^{D2} \sum_{d1=0}^{D1} \sum_{ch=0}^{Ch} R2(s, d2, y, x) \times R1(d2, d1, y, x) \times R0(d1, ch, y, x)$$

R: Degree of contribution of the input image to the identification result
R2: Degree of contribution of the second layer local feature amount F2 to the identification result
R1: Degree of contribution of the first layer local feature amount F1 to R2
R0: Degree of contribution of the input image to R1
s: State number (0, 1, ..., S)
y: Vertical position (0, 1, ..., Y)
x: Horizontal position (0, 1, ..., X)
d2: Second layer feature amount number (0, 1, ..., D2)
d1: First layer feature amount number (0, 1, ..., D1)
ch: Channel of the input image (0, 1, ..., Ch)

Thereby, the reaction value calculating unit 204 calculates the reaction value R which is the degree of contribution of the input image to each identification result. This is an exemplary reaction value calculation method.

Note that, at any step in the above-mentioned reaction value calculation method, a normalization process or a thresholding process, an emphasizing process, a blurring process, or the like may be applied to values for the degrees of contribution R2, R1, R0 or a result of multiplication of them in order to enhance the visibility of reaction values.

Although, in the present embodiment explained, calculation of local feature amounts is performed at two layers, reaction values can be obtained similarly using three or more layers.

Next, the reaction value difference calculating unit 205 is explained. The reaction value difference calculating unit 205 uses reaction values for a plurality of states input from the reaction value calculating unit 204 to obtain differences between the reaction value based on reaction value specifying information input through the user interface unit 206.

Figure 6:
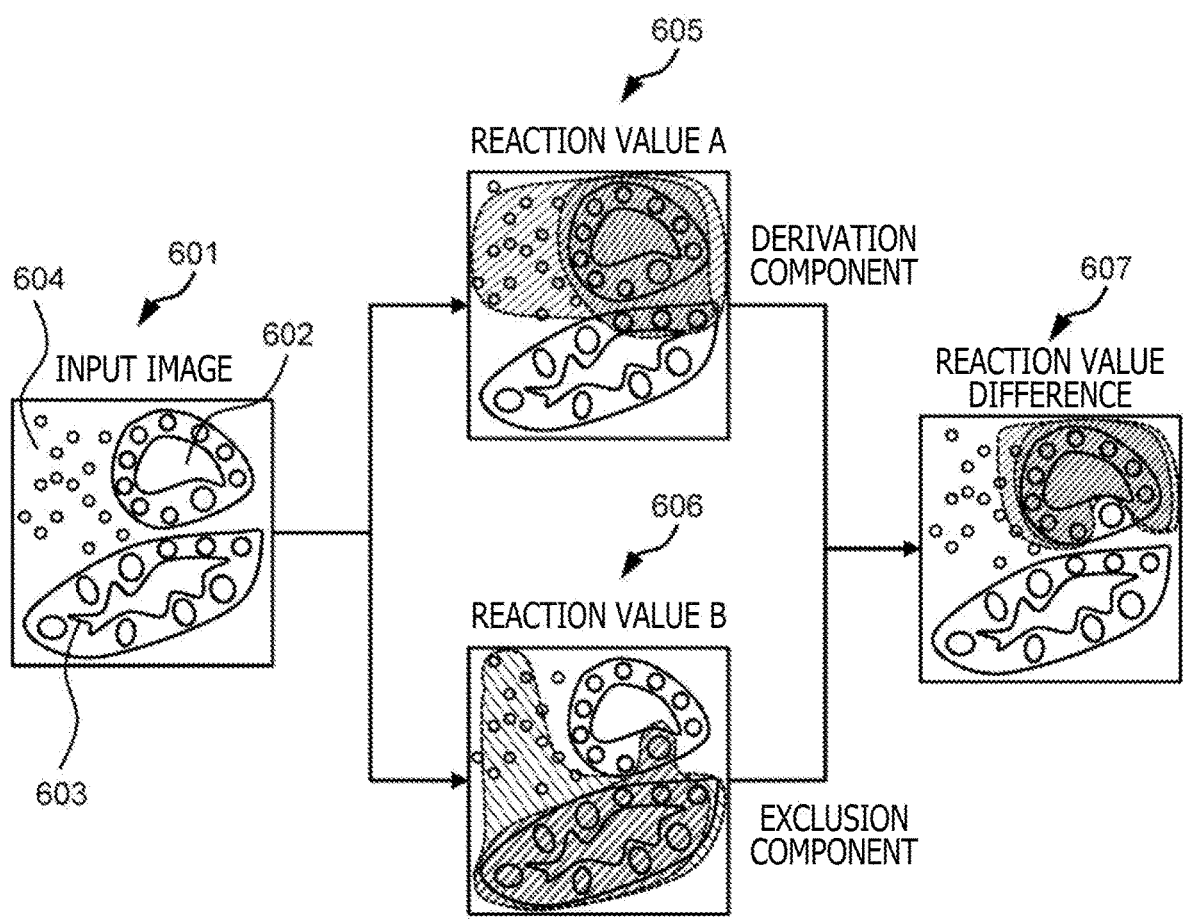
FIG. 6 depicts exemplary reaction value and reaction value difference calculation.

FIG. 6 depicts exemplary calculation of a reaction value difference. An input image 601 includes a state A tissue 602, a state B tissue 603 and interstitium 604. A reaction value A605 is a reaction value corresponding to the state A, and a reaction value B606 is a reaction value corresponding to the state B. A reaction value difference 607 depicts a result obtained by subtracting the reaction value B606 from the reaction value A605.

The shading in the reaction value A605, reaction value B606 and reaction value difference 607 indicates areas with positive reaction values, and the darker the shading is, the larger the reaction value is. On the other hand, portions without shading indicate areas where reaction values are equal to or lower than 0 or are close to 0.

Cell and tissue images include common features among different states of cells and tissues. For example, the interstitium 604 depicted in FIG. 6 appears often around tissues irrespective of the states of the tissues. Because of this, if a feature is determined using so-called machine learning or statistical techniques, the portions of interstitium 604 tend to have reaction values that are analogous to both the states A and B, and reaction values occur in common areas even if they are reaction values corresponding to different states like the reaction value A605 and reaction value B606 in FIG. 6. On the other hand, the area of the state A tissue 602 has a larger reaction value A605, and the area of the state B tissue 603 has a larger reaction value B606.

Calculating the reaction value difference 607 allows exclusion of common components of reaction values. The reaction value difference 607 in FIG. 6 represents a result obtained by subtracting the reaction value B606 from the reaction value A605, the reaction value A605 at this time is called a derivation component, and the reaction value B606 at this time is called an exclusion component. Since the reaction value A605 and the reaction value B606 are approximately the same in the interstitium 604, it has a value close to 0 in the reaction value difference 607. Since, in the state B tissue 603, the reaction value B606 is larger than the reaction value A605, it has a negative value in the reaction value difference 607.

On the other hand, since, in the state A tissue 602, the reaction value A605 is larger than the reaction value B606, it has a positive reaction value. Thereby, it becomes possible to exclude areas with features that are common to a plurality of states, and selectively display an area that is likely to be in each state.

The reaction value difference information may be obtained from three or more reaction values. Specifically, there are techniques in which a result of combining a plurality of reaction values is subtracted from one reaction value, one reaction value is subtracted from a result of combining a plurality of reaction values, and a result of combining a plurality of reaction values is subtracted from a result of combining a plurality of reaction values. Combining is addition, multiplication, obtaining the logical sum, obtaining the logical product or the like, and some function may be applied to each element of a result of combining.

Although, in FIG. 6, only a portion where the reaction value is positive is depicted in the reaction value difference 607, a portion where the reaction value is negative may be displayed simultaneously by performing a process such as switching display colors between the portion where the reaction value is positive and the portion where the reaction value is negative. In this case, the portion where the reaction value is negative in the reaction value difference 607 is an area where a result of subtracting the reaction value A605 from the reaction value B606 is a positive value, and by displaying it together with the reaction value difference 607, the reaction value difference information about two states can be displayed simultaneously.

In addition, in another technique, a color may be allocated to each state in advance for three or more reaction values, and the reaction value difference calculating unit 205 may calculate, for each pixel, the reaction value difference information treating a reaction value with the largest value as a derivation component, and a reaction value with the second largest value as an exclusion component. In this case, the display unit 207 may display three or more pieces of reaction value difference information simultaneously by a method such as displaying reaction value difference information in a color allocated to each state to be treated as a derivation component.

Figure 7:
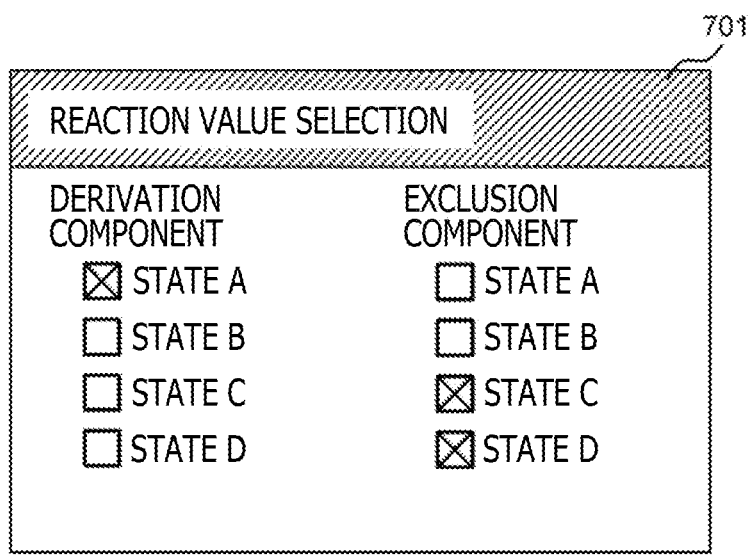
FIG. 7 depicts a reaction value selection GUI.

FIG. 7 depicts an exemplary GUI related to selection of reaction values to be used in calculation of reaction value difference information. In the example depicted in FIG. 7, the number of states to be identified is four, and includes a state A to a state D. In a window 701, checkboxes or the like are arranged for selection of derivation components and exclusion components. In this example, while a reaction value corresponding to the state A is a derivation component, a result of combining reaction values corresponding to the state C and the state D is an exclusion component.

Triggered by a change in selection contents depicted in FIG. 7, the display unit 207 switches a display result depicted in FIG. 6, and displays specified reaction value difference information on the image display apparatus 105. In this manner, the states of cells or tissues can be visualized at accurate positions, and diagnostic assistance to pathologists becomes possible.

(2) Second Embodiment

In order to improve visibility, it is commonly practiced in cell or tissue diagnosis to stain cells or tissues using chemicals for staining cells or tissues. However, nonuniformity occurs in staining shade depending on degradation of chemicals or staining methods in some cases, and unless a feature amount calculation method or an identification method corresponding to staining shade is used, the accuracy of identification of the state of cells or tissues might lower, errors in a result of visualization of the state of cells or tissues might occur, and so on.

The second embodiment relates to a method and an apparatus that perform identification according to staining shade, and, based on a result of it, perform visualization of the state of cells or tissues by automatically classifying cell or tissue images with different staining shade. Thereby, even if there is nonuniformity in staining shade in cell or tissue images, accurate visualization of the state of cells or tissues can be performed, and diagnostic assistance to pathologists becomes possible.

Note that since, in the second embodiment, the hardware configuration is similar to that in the first embodiment, the explanation about FIG. 1 applies here also, but is omitted here.

Figure 8:
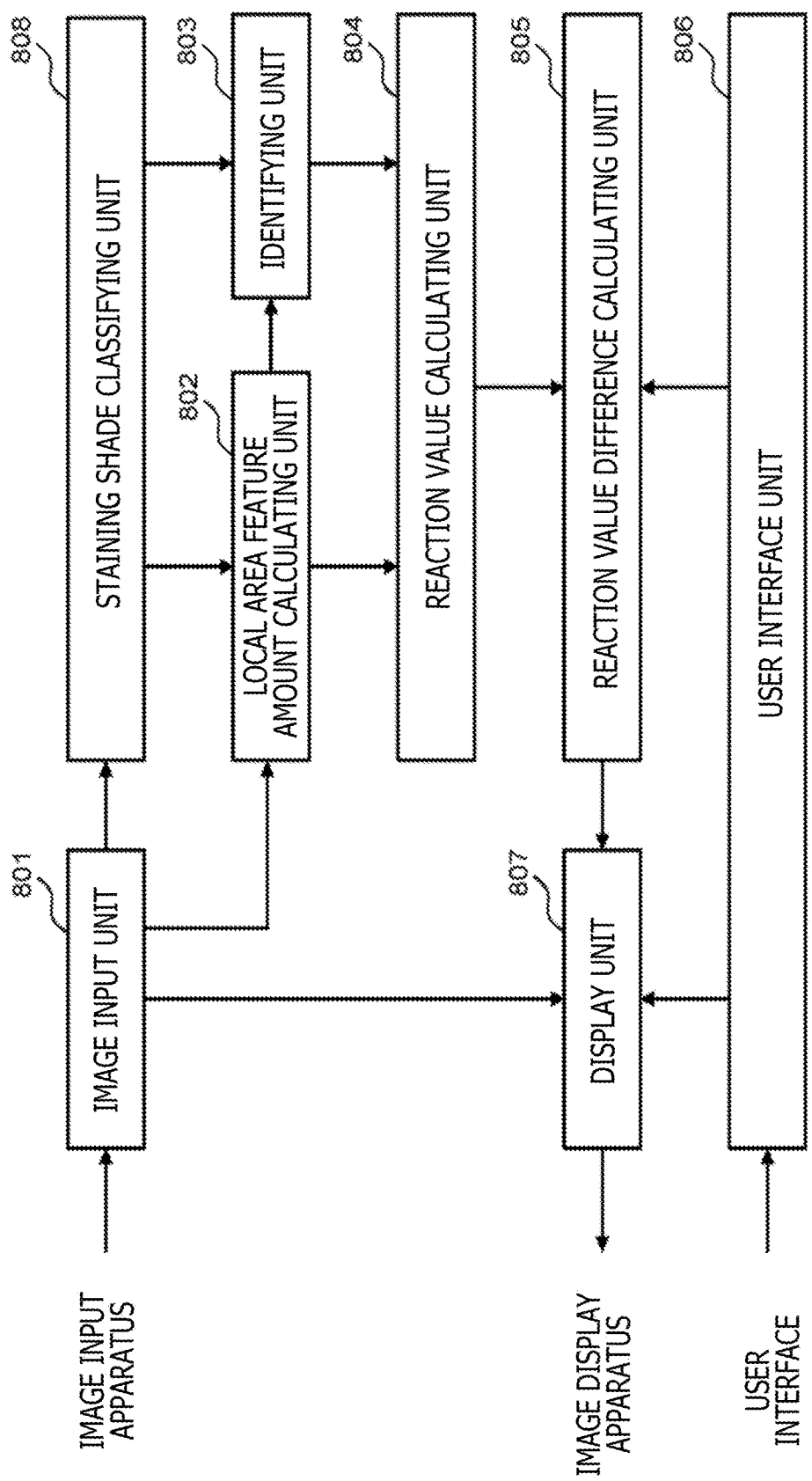
FIG. 8 is a block diagram of the arithmetic operation apparatus according to a second embodiment.

FIG. 8 depicts functional blocks of the image diagnosis assisting apparatus. Since an image input unit 801, a reaction value calculating unit 804, a reaction value difference calculating unit 805, a user interface unit 806 and a display unit 807 in the second embodiment are similar to the image input unit 201, reaction value calculating unit 204, reaction value difference calculating unit 205, user interface unit 206 and display unit 207 in FIG. 2 in the first embodiment, respectively, explanations thereof are omitted.

The staining shade classifying unit 808 classifies, for each degree of staining shade, cell or tissue images input through the image input unit 801, and outputs a result of the classification to the local area feature amount calculating unit 802 or the identifying unit 803, or to both the local area feature amount calculating unit 802 and the identifying unit 803. Although, in the present embodiment explained, as one example, the result is output to both the local area feature amount calculating unit 802 and the identifying unit 803, in one manner, the destination of output may be switched to either of them.

The local area feature amount calculating unit 802 calculates feature amounts of local areas for the image input through the image input unit 801. At this time, the local area feature amount calculating unit 802 switches from one feature amount calculation method to another based on the staining shade classification result input from the staining shade classifying unit 808.

The identifying unit 803 has a plurality of identifying devices (not illustrated), and uses the local area feature amounts output by the local area feature amount calculating unit 802 to output a result of identification of a plurality of states. At this time, the identifying unit 803 switches from one identification method to another based on the staining shade classification result input from the staining shade classifying unit 808.

The staining shade classifying unit 808 is explained. The staining shade classifying unit 808 automatically classifies, for each degree of staining shade, cell or tissue images input through the image input unit 801. Here, an exemplary staining shade classification method is explained.

The staining shade classifying unit 808 has one or more evaluation indices for classifying staining shade. The evaluation indices used include the average value or variance of respective RGB channels for an input image, a value obtained through conversion of the average value or variance by principal component analysis, or the like.

Figure 9:
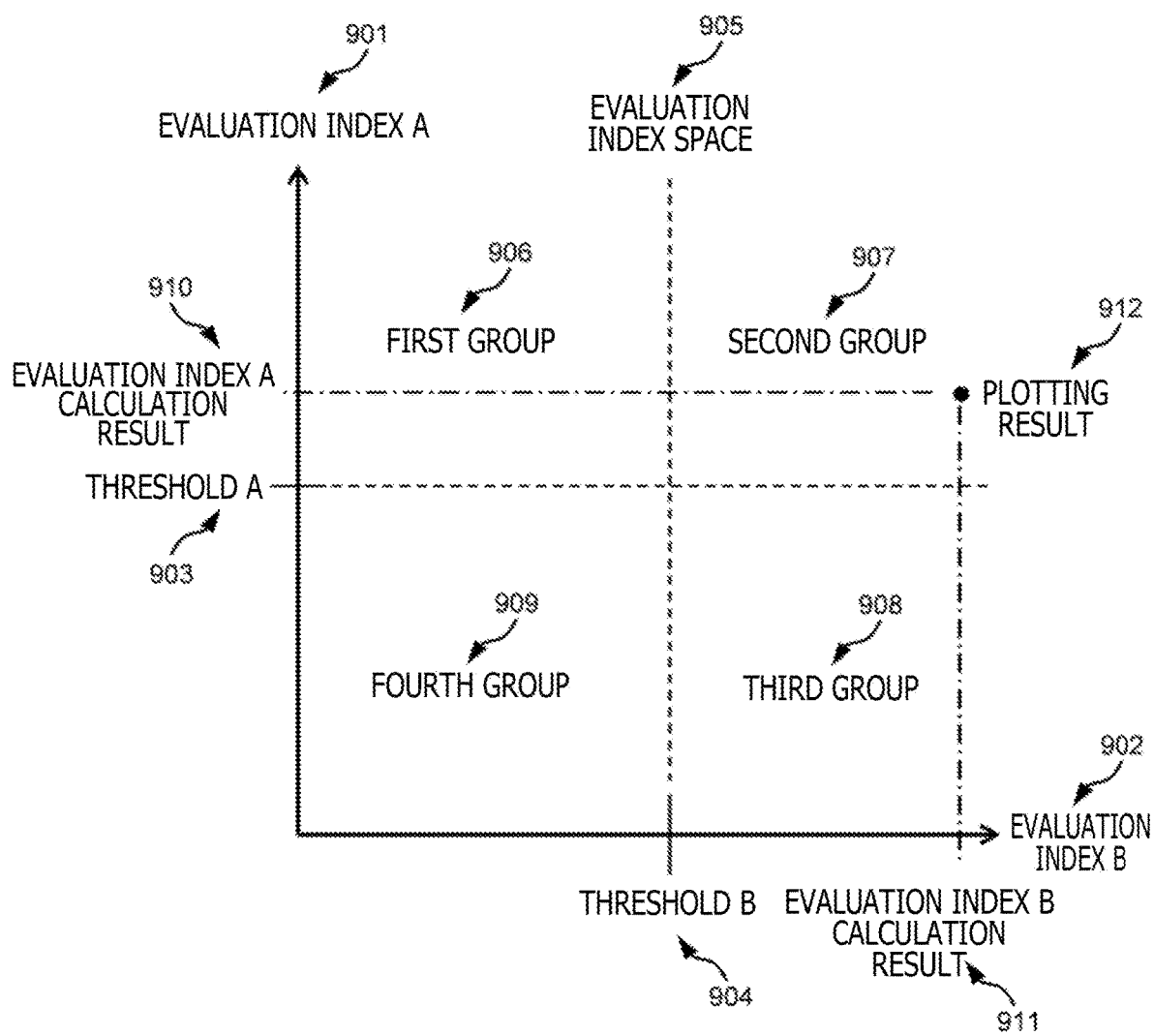
FIG. 9 depicts an exemplary staining shade classification method.

FIG. 9 depicts an exemplary staining shade classification method. The illustrated example depicts the case where two evaluation indices, an evaluation index A901 and an evaluation index B902, are used. A space formed by a plurality of evaluation indices is defined as an evaluation index space 905. The evaluation index A901 and the evaluation index B902 are each divided into two sections by a threshold A903 and a threshold B904, respectively. The combination of the sections of the evaluation index A901 and the evaluation index B902 divides the evaluation index space 905 into a first group 906, a second group 907, a third group 908 and a fourth group 909. Hereinafter, these groups are called "staining shade groups."

Upon receiving an input of an input image at the staining shade classifying unit 808, the staining shade classifying unit 808 calculates respective numerical values for the evaluation index A901 and evaluation index B902. The evaluation index A901 and evaluation index B902 are calculated by using Formula (7A) and Formula (7B) like the ones depicted below.

$$A(ave_{RGB}, var_{RGB}) = \alpha_1 \times PCA_a(ave_{RGB}, var_{RGB}) + \alpha_2 \times PCA_b(ave_{RGB}, var_{RGB}) \quad (7A)$$

$$B(ave_{RGB}, var_{RGB}) = \beta_1 \times PCA_c(ave_{RGB}, var_{RGB}) + \beta_2 \times PCA_d(ave_{RGB}, var_{RGB}) \quad (7B)$$

A: Evaluation index A
B: Evaluation index B
aveRGB: Average value of respective RGB channels of the input image
varRGB: Variance of respective RGB channels of the input image
PCAa: Any principal component a of the average value and variance of RGB
PCAb: Any principal component b of the average value and variance of RGB
PCAc: Any principal component c of the average value and variance of RGB
PCAd: Any principal component d of the average value and variance of RGB
$\alpha_1$: Coefficient by which PCAa is multiplied
$\alpha_2$: Coefficient by which PCAb is multiplied
$\beta_1$: Coefficient by which PCAc is multiplied
$\beta_2$: Coefficient by which PCAd is multiplied A result of analysis of principal components of the average value aveRGB and variance varRGB of respective RGB channels of the input image is defined as "PCA," and any principal components are defined as PCAa, PCAb, PCAc and PCAd.

In the example of Formula (7A) and Formula (7B), a numerical value obtained by multiplying the principal component PCAa and principal component PCAb by the coefficients $\alpha_1$ and $\alpha_2$, respectively, and summing the resultant values is used as the evaluation index A901, and a numerical value obtained by multiplying the principal component PCAc and principal component PCAd by the coefficients $\beta_1$ and $\beta_2$, respectively, and summing the resultant values is used as the evaluation index B902.

An exemplary result of calculation of the evaluation index A of the input image is depicted as an evaluation index A calculation result 910. Likewise, an exemplary result of calculation of the evaluation index B is depicted as an evaluation index B calculation result 911. In addition, a result of plotting the evaluation index A calculation result 910 and evaluation index B calculation result 911 on the evaluation index space 905 is depicted as a plotting result 912.

In the example of FIG. 9, staining shade is classified based on in which staining shade group in the evaluation index space 905 a result is plotted. Since, in the example of the plotting result 912, the result is plotted in the second group 907, the classification result is the second group 907. The staining shade classifying unit 808 outputs, as a staining shade classification result, the result of classification of the staining shade of an input image by the above-mentioned method.

Although, in FIG. 9, the evaluation index space 905 is divided based on a threshold for each evaluation index, the evaluation index space 905 may be divided by another technique such as setting a plurality of representative points in the evaluation index space 905 and classifying results based on distances from the representative points. Note that the thresholds for evaluation indices or the like may be fixed values or may be determined dynamically based on a distribution on the evaluation index space.

Next, the local area feature amount calculating unit 802 is explained. The local area feature amount calculating unit 802 uses weights stored in the memory 102 to extract local area feature amounts such as the color, luminance or shape in each pixel or small area in an input image.

Although the local area feature amount calculation method in the second embodiment is similar to the calculation method used by the local area feature amount calculating unit 202 in the first embodiment, it is different from the first embodiment in that the weight for local area feature amount extraction is switched from one to another according to staining shade.

Weights for local area feature amount calculation for each staining shade group or a weight for local area feature amount calculation to be the basis are/is stored in the memory 102. By a method such as switching the weight from one to another or converting the weight according to a staining shade classification result, the weight for local area feature amount calculation is switched from one to another according to staining shade.

Using the weight, the local area feature amount calculating unit 802 calculates a local area feature amount corresponding to a staining shade classification result. Note that although, in the present embodiment, it is assumed that weights to be used in local area feature amount calculation are weights learned through machine learning, the weights may be updated using input images by techniques such as so-called unsupervised learning, for example. Furthermore, the above-mentioned updating of the weights is not limited to that executed in an apparatus, but may be performed in a manner such as sending information to a server or the like via a communication apparatus and receiving a result of updating performed at the server.

Next, the identifying unit 803 is explained. The identifying unit 803 uses weights stored in the memory 102 to perform identification of a plurality of states based on local area feature amounts output by the local area feature amount calculating unit 802.

Although the identification method in the second embodiment is similar to the identification method used by the identifying unit 203 in the first embodiment, it is different from the first embodiment in that the weight for identification is switched from one to another according to staining shade.

Weights for identifying a plurality of states of cells or tissues for each staining shade group or a weight for identifying a plurality of states of cells or tissue to be the basis are/is stored in the memory 102. By a method such as switching the weight from one to another or converting the weight according to a staining shade classification result, the weight for identifying a plurality of states of cell or tissues is switched from one to another according to staining shade.

Note that although, in the present embodiment, the weights for identifying a plurality of states of cells or tissues for each staining shade group are prepared already through machine learning or the like beforehand, the weights may be updated using input images by a technique such as semi-supervised learning, for example. Furthermore, the above-mentioned updating of the weights is not limited to that executed in an apparatus, but may be performed in a manner such as sending information to a server or the like via a communication apparatus and receiving a result of updating performed at the server.

Using the weights, the identifying unit 803 performs identification according to a staining shade classification result output by the staining shade classifying unit 808.

In the above-mentioned manner, feature extraction and identification coping with nonuniformity in staining shade of input images become possible. Thereby, even if there is nonuniformity in staining shade in input images, the states of cells or tissues can be visualized at accurate positions, and diagnostic assistance to pathologists becomes possible.

(3) Third Embodiment

The third embodiment employs a sample analyzing system that collects samples using a microdissection sample collecting apparatus or another type of sample collecting apparatus and performs analysis using an analyzing apparatus such as a mass analyzing apparatus or a DNA sequencer, for example, based on information about cells or tissue states obtained through the method described in the first embodiment or second embodiment.

Figure 11:
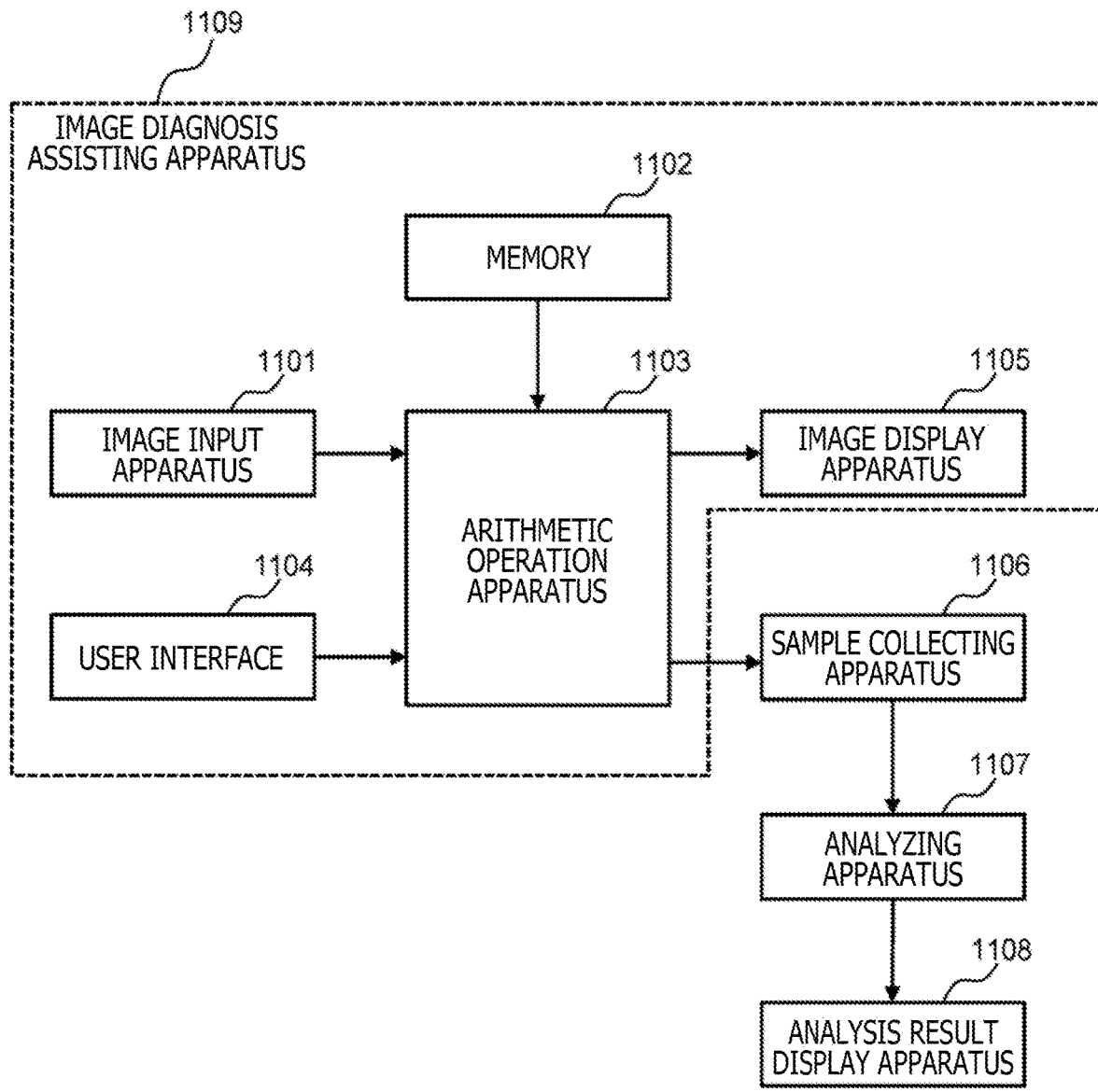
FIG. 11 is a system configuration diagram according to a third embodiment.

FIG. 11 depicts an exemplary configuration of the sample analyzing system according to the third embodiment. Similar to the configuration of the embodiments mentioned already, an image diagnosis assisting apparatus 1109 includes an image input apparatus 1101, a memory 1102, an arithmetic operation apparatus 1103, a user interface 1104 and an image display apparatus 1105. That is, since these image input apparatus 1101, memory 1102, arithmetic operation apparatus 1103, user interface 1104 and image display apparatus 1105 include the image input apparatus 101, memory 102, arithmetic operation apparatus 103, user interface 104 and image display apparatus 105 in the first embodiment and second embodiment, respectively, and perform similar operation, explanations thereof are omitted.

Furthermore, the sample analyzing system according to the third embodiment includes a sample collecting apparatus 1106, an analyzing apparatus 1107 and an analysis result display apparatus 1108. The sample collecting apparatus 1106 performs sample collection based on reaction value difference information output from the image diagnosis assisting apparatus 1109. The analyzing apparatus 1107 receives samples collected by the sample collecting apparatus 1106 and performs analysis. The analysis result display apparatus 1108 is a display or a printer that displays a result of analysis performed by the analyzing apparatus 1107, for example.

Figure 12:
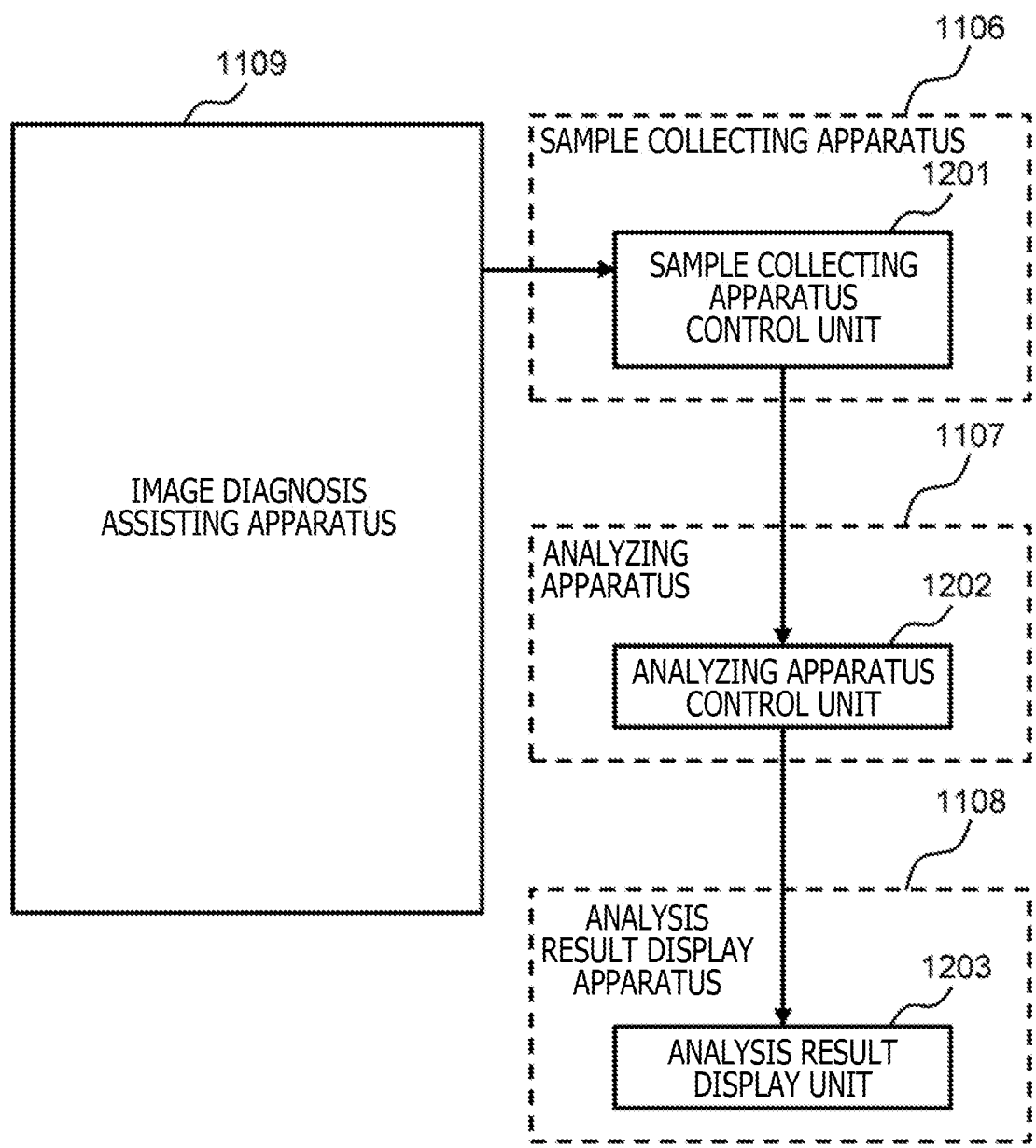
FIG. 12 is a block diagram of a system according to the third embodiment.

FIG. 12 depicts functional blocks of the sample analyzing system according to the third embodiment. The image diagnosis assisting apparatus 1109 has a similar configuration as that of the image diagnosis assisting apparatus 100 described in the first embodiment or second embodiment.

The sample collecting apparatus control unit 1201 determines a sample-collected area based on reaction value difference information output by the image diagnosis assisting apparatus 1109, and collects samples. The analyzing apparatus control unit 1202 performs analysis of the samples based on a sample collection condition input from the sample collecting apparatus control unit 1201. The analysis result display unit 1203 receives a result of analysis performed by the analyzing apparatus control unit 1202 and displays the result of analysis.

The sample collecting apparatus control unit 1201 is explained in detail. The sample collecting apparatus control unit 1201 receives the reaction value difference information mentioned already from the image diagnosis assisting apparatus 1109, and determines a sample-collected area. Methods of determining a sample-collected area include, for example: determining, as a sample-collected area, an area where reaction value difference information exceeds a threshold; and normalizing reaction value difference information and determining, as a sample-collected area, an area with a certain size out of an area with a high value.

The analyzing apparatus control unit 1202 receives a collected sample from the sample collecting apparatus control unit 1201, and performs analysis of the sample. The analysis result display unit 1203 receives a result of analysis of the sample from the analyzing apparatus control unit 1202, and presents the result of analysis to a user via the analysis result display apparatus 1108.

Thereby, it becomes possible to provide a user with an analyzing system that performs all through from sample collection to sample analysis based on information of cell or tissue states output by the image diagnosis assisting apparatus described in the first embodiment or second embodiment.

(4) Other Embodiments

The above-mentioned embodiments are examples for explaining the present invention, and it is not aimed to limit the present invention only to these embodiments. The present invention can be implemented in various forms as long as such forms do not deviate from the aim of the present invention. For example, although various types of program processes are explained sequentially in the above-mentioned embodiments, the present invention is not particularly confined to it. Accordingly, as long as contradictions do not occur in a processing result, in one configuration, the order of the processes may be rearranged, or operation of the processes may be performed in parallel.

REFERENCE SIGNS LIST

202: Local area feature amount calculating unit
203: Identifying unit
204: Reaction value calculating unit
205: Reaction value difference calculating unit
1106: Sample collecting apparatus
1107: Analyzing apparatus 1108: Analysis result display apparatus
1109: Image diagnosis assisting apparatus
1201: Sample collecting apparatus control unit
1202: Analyzing apparatus control unit
1203: Analysis result display unit

The invention claimed is:

1. An image diagnosis assisting apparatus comprising:
a local area feature amount calculating unit that calculates a local area feature amount from an input image, wherein the local area feature amount is a three-dimensional array with dimensions including a feature amount number, a vertical position, and a horizontal position;
an identifying unit that performs a plurality of identification processes using the local area feature amount, including identifying a plurality of states of cells or tissues in the input image and a likelihood of each state;
a reaction value calculating unit that calculates a plurality of reaction values indicating a degree of contribution of each dimension of the local area feature amount to each identification result, based on which unit area in the input image each identification result is judged, using a calculation result of the local area feature amount and a result of the plurality of identification processes; and
a reaction value difference calculating unit that calculates differences between the plurality of reaction values.

2. The image diagnosis assisting apparatus according to claim 1, including:
a staining shade classifying unit that classifies the input image according to staining shade before the local area feature amount calculating unit calculates the local area feature amount from the input image.

3. The image diagnosis assisting apparatus according to claim 1 wherein
the local area feature amount calculating unit updates a coefficient group to be used in calculation of a local area feature amount from the input image or a coefficient group to be used in a plurality of identification processes using the local area feature amount.

4. An image diagnosis assisting method comprising:
a local area feature amount calculation step of calculating, by an arithmetic operation unit, a local area feature amount from an input image, wherein the local area feature amount is a three-dimensional array with dimensions including a feature amount number, a vertical position, and a horizontal position;
an identification step of performing, by the arithmetic operation unit, a plurality of identification processes using the local area feature amount, including identifying a plurality of states of cells or tissues in the input image and a likelihood of each state;
a reaction value calculation step of calculating, by the arithmetic operation unit, a plurality of reaction values indicating a degree of contribution of each dimension of the local area feature amount to each identification result, based on which unit area in the input image each identification result is judged, using a calculation result of the local area feature amount and a result of a plurality of identification processes; and
a reaction value difference calculation step of calculating, by the arithmetic operation unit, differences between a plurality of reaction values,
wherein the local area feature amount is a three-dimensional array with dimensions including a feature amount number, a vertical position, and a horizontal position.

5. The image diagnosis assisting method according to claim 4, including:
a staining shade classification step of classifying, by the arithmetic operation unit, the input image according to staining shade before the local area feature amount is calculated from the input image by the arithmetic operation unit at the local area feature amount calculation step.

6. The image diagnosis assisting method according to claim 4, including:
an update step of updating, by the arithmetic operation unit, a coefficient group to be used in calculation of the local area feature amount from the input image or a coefficient group to be used in a plurality of identification processes using the local area feature amount.

7. A sample analyzing system comprising:
a local area feature amount calculating unit that calculates a local area feature amount from an input image, wherein the local area feature amount is a three-dimensional array with dimensions including a feature amount number, a vertical position, and a horizontal position;
an identifying unit that performs a plurality of identification processes using the local area feature amount, including identifying a plurality of states of cells or tissues in the input image and a likelihood of each state;
a reaction value calculating unit that calculates a plurality of reaction values indicating a degree of contribution of each dimension of the local area feature amount to each identification result, based on which unit area in the input image each identification result is judged, using a calculation result of the local area feature amount and a result of the plurality of identification processes;
a reaction value difference calculating unit that calculates differences between the plurality of reaction values;
a sample collecting unit that collects a sample based on the calculated information; and
an analyzing unit that performs analysis of the sample collected by the sample collecting unit,
wherein the local area feature amount is a three-dimensional array with dimensions including a feature amount number, a vertical position, and a horizontal position.

8. The sample analyzing system according to claim 7, including:
a staining shade classifying unit that classifies the input image according to the staining shade before the local area feature amount calculating unit calculates the local area feature amount from the input image.

9. The sample analyzing system according to claim 7, wherein
the local area feature amount calculating unit updates a coefficient group to be used in calculation of a local area feature amount from the input image or a coefficient group to be used in a plurality of identification processes using the local area feature amount.

* * * * *